United States Patent [19]

Holovka et al.

[11] 4,169,110

[45] Sep. 25, 1979

[54] CONDENSATION AND TRIMERIZATION OF ALDEHYDES

[75] Inventors: John M. Holovka, Englewood; Edward Hurley, Jr., Littleton, both of Colo.

[73] Assignee: Marathon Oil Company, Findlay, Ohio

[21] Appl. No.: 12,426

[22] Filed: Feb. 18, 1970

[51] Int. Cl.² ............................................. C07C 47/20
[52] U.S. Cl. ................................................ 260/601 R
[58] Field of Search .................................... 260/601 R

[56] References Cited

U.S. PATENT DOCUMENTS

| | | | |
|---|---|---|---|
| 2,982,784 | 5/1961 | Re ck et al. | 260/601 R |
| 3,148,218 | 9/1964 | Heimsch et al. | 260/601 R |

FOREIGN PATENT DOCUMENTS 1007987 10/1965 United Kingdom ................ 260/533 C

OTHER PUBLICATIONS

Eidus et al., Chemical Abstracts, vol. 65, col. 5356d, 1966.
Chemical Abstracts, vol. 73, 14190f, Alekseeva, et al.

*Primary Examiner*—Werren B. Lone
*Attorney, Agent, or Firm*—Joseph C. Herring; Jack L. Hummel

[57] ABSTRACT

Group VIII metal salts such as iridium chloride and rhodium chloride are used as catalysts in the condensation reactions of aldehydes to produce acetals and alpha,beta-unsaturated aldehydes. These catalysts are also useful in the conversion of aldehydes to trioxanes. Materials of this type are widely used in the formation of resins, preservatives, dyes, and chemical intermediates.

2 Claims, No Drawings

CONDENSATION AND TRIMERIZATION OF ALDEHYDES

BACKGROUND OF THE INVENTION

1. Field of the Invention

This invention relates to the self-condensation of aldehydes, the condensation of aldehydes with alcohol, the trimerization of aldehydes to produce alpha,beta-unsaturated aldehydes, acetals, and trioxanes respectively and the conversion of trioxanes to aldehydes in the presence of catalytic amounts of Group VIII metal salts.

Aldehydes, trioxanes, and acetals are widely used in the formation of resins, preservatives, dyes, and chemical intermediates.

Various acids and bases have been used as catalysts for such condensation reactions. Since alcohol dehydration is catalyzed by acids but not by bases, in a number of such cases the final result of the condensation may be determined by the nature of the catalyst used. Thus some base-catalyzed condensations are much more likely to stop at the stage of the aldol than is an acid catalyzed condensation.

The present invention describes a new process for the preparation of acetals, trioxanes, and alpha,beta-unsaturated aldehydes. This process is characterized by low temperature, liquid phase, homogeneously catalyzed reactions of aldehydes in the presence of Group VIII metal salt catalysts.

2. Description of the Prior Art

The acid- and base-catalyzed aldol condensations of aldehydes, as well as the acid-catalyzed condensation of aldehydes with alcohols, are well-known reactions and discussions concerning these reactions may be found in introductory organic chemistry text books. The following references are of special interest in that they teach high temperature, (i.e. 600°–800° F.) vapor phase, or heterogeneously catalyzed reactions wherever Group VIII metals are employed as catalysts for these reactions.

| Aldol Condensations of Aldehydes | | |
|---|---|---|
| Reference | Catalyst | Conditions[a] |
| 1) U.S. 2,549,508 | $Fe_2O_3$ | V, 700° F. |
| 2) Ciola, R., Anais Assoc. Brasil., 20, 63–76 (1961). | $Cd(PO_4)_2$ $Ni_3(PO_4)_2$ | V, 275° C. |
| 3) Nodzu, R., et al., J. Chem. Soc. Japan, 57, 914–16 (1954). | $Fe(OH)_3$ $Ni(OH)_2$ | V, 170°–260° C. |
| 4) Dolgov, B. N., et al., Zhur., Obshchei Khim., 22, 950-3 (1952). | $Al_2O_3$—$Fe_2O_3$ | V, 400° C. |
| Condensation of Aldehydes with Alcohols | | |
| 1) Brit. 607,130 | $NH_4Cl$ | C, 25° C. |
| 2) U.S. 2,451,949 | Bauxite fuller's earth | V, 0–50° C. |
| 3) Fr. 868,182 | $H^+$ + $CaCl_2$ | C — |
| 4) Brit. 625,131 | $H_2SO_4$ | C, 15–20° C. |
| 5) U.S. 2,519,540 | $H_2SO_4$ | C, 20° C. |
| 6) U.S. 2,691,684 | none | V, 350° C. |
| 7) Brit. 716,541 | HCl | C, 65° C. |
| 8) U.S. 2,782,177 | Ni | — |
| 9) U.S. 2,566,559 | Cation exchange resin | C, 30° C. |

[a] C = condensed phase, V = vapor phase

SUMMARY OF THE INVENTION

It has been found that Group VIII metal salts will catalyze the cyclotrimerization of aldehydes to trioxanes. At higher temperatures, these catalysts promote the reverse reaction, i.e., the conversion of trioxanes to aldehydes. With prolonged treatment, the aldehydes self-condense to give alpha,beta-unsaturated aldehydes. In general such reactions can be characterized by:

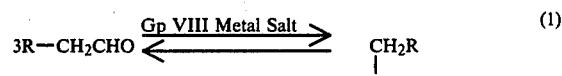

When aldehydes are treated with Group VIII metal salts in alcohol solution at room temperature, a rapid reaction (5 min) affords high yields (50–95%) of acetals (III). This reaction can be characterized by:

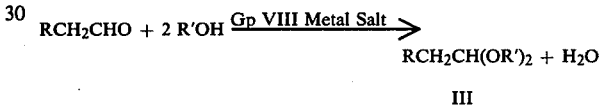

For the purposes of these reactions, R and R' are selected from either linear or branched-chain alkyl groups having twelve or fewer carbon atoms. The molecules formed by such alkyl groups should be liquids under the conditions of the reaction.

These reactions should be run in the absence of $O_2$ as aldehydes are often oxidized to acids in the presence of $O_2$.

Utility of the Invention

The products of this invention may be used as tanning agents, intermediates for n-butyl alcohol, polyvinyl acetals, as well as in the synthesis of rubber chemicals. See, *The Condensed Chemical Dictionary*, pp. 315 and 944.

DESCRIPTION OF THE PREFERRED EMBODIMENTS

Starting Materials

The starting materials of these reactions are characterized by the formula $RCH_2CHO$ wherein the R group is hydrogen or a linear or branched-chain molecule having 12 or fewer carbon atoms or mixtures thereof. Examples of such compounds are acetaldehyde, propionaldehyde, isobutyl aldehyde, acrolein, caproaldehyde and the like. Substituents may be present on the R group so long as they are substantially non-interfering with the reactions taught in this invention. The number of carbon atoms per alkyl group is preferably from 1 to 12, more preferably from 1 to 7, and most preferably from 1 to 4.

The reactions involving the aldehydes, trioxanes, and acetals of this invention are conducted in the liquid phase. The reaction is one of homogeneous catalysis, that is, where a catalyst, herein defined, is so dispersed within the reaction media that no gross interface exists between the catalyst and the reactants.

Catalysts

The catalysts of the present invention are Group VIII metal salts which at least partially dissociate, preferably to a substantial degree, in the reaction media to give an active catalyst species.

Useful Group VIII metal salts include salts of iron, exemplified by basic ferric acetate, ferricammonium oxalate, ferric arsenate, ferric benzoate, ferric bromide, anhydrous ferric chloride, ferric chromate, ferric dichromate, ferric hydroxide, ferric nitrate, ferric phosphate, ferric succinate, ferric sulfate, ferrous acetate, ferrous ammonium sulfate, ferrous chloride, and the like; ruthenium salts exemplified by ruthenium chloride, ruthenium red, and the like; osmium salts, exemplified by osmium ammonium chloride, osmium potassium chloride, and the like; cobaltous salts exemplified by cobaltous acetate, cobaltous ammonium sulfate, cobaltous arsenate, cobaltous bromate, cobaltous bromide, cobaltous carbonate, cobaltous chromate, cobaltous formate, cobaltous hydroxide, cobaltous iodide, cobaltous nitrate, cobaltous phosphate, cobaltous sulfate, and the like; rhodium salts exemplified by rhodium chloride, rhodium nitrate, rhodium sulfate, and the like; iridium salts exemplified by iridic bromide, iridic chloride, iridic iodide, and the like; nickel salts exemplified by nickelous ammonium chloride, nickel ammonium nitrate, nickelous acetate, nickelous bromide, nickelous citrate, basic nickel carbonate, nickel iodide, nickel nitrate, nickelous sulfate and the like; palladium salts exemplified by palladium chloride, palladium acetate, palladium nitrate, palladium sodium chloride, palladium sulfate, and the like; and platinum salts exemplified by platinum chloride and the like.

Preferred Group VIII metal salts are those of rhodium, ruthenium, and palladium in descending order of preference. The most preferred anions are the acetates and nitrates which are at least partially soluble in the reaction media.

Normally the amounts of catalysts are not critical to the reaction. Excess amounts of catalysts are not preferred because of economic considerations but in most instances for every mole of aldehyde or trioxane starting material preferably from about 0.00001 to about 0.1 moles of catalyst are used, more preferably from about 0.0001 moles to about 0.05 moles are used and most preferably from about 0.001 to about 0.01 moles are used. Neither are the ratios of aldehyde and alcohol starting materials critical to the reaction but in most instances for every mole of aldehyde starting material preferably from about 0.01 to about 1000 moles of alcohol are used, more preferably from about 0.1 to about 100 moles, and most preferably from about 1 to about 10 moles of alcohol are used.

Temperature:

Temperature conditions are important to the embodiments of this invention since the type of reaction, i.e. cyclotrimerization, self-condensation, etc. are more favorably carried out in certain temperature ranges. These reactions are preferably conducted in the overall range of about $-20°$ C. to about 300° C.

The cyclotrimerization of aldehydes to trioxanes is preferably carried out in the range of from about $-20°$ to about 80° C., more preferably from about 0° to about 45° C., and most preferably from about 15° to about 30° C. Examples 5, 6 and 9 in the Table of Results show this temperature relation.

At higher temperatures, of about 80° to 250° C., the Group VIII metal salt catalysts promote the reverse reaction, i.e., the conversion of trioxanes to aldehydes as shown by Example 7 of the Table of Results. More preferably this reaction is carried out in the range of from about 80° to about 150° C. and most preferably from about 90° to about 120° C. With prolonged treatment at these higher temperatures (1–24 hours), the aldehydes self-condense to give alpha,beta-unsaturated aldehydes of the type shown in examples 5, 7 and 10. When aldehydes are treated with Group VIII metal salts in alcohol solution at about $-20°$ to 150° C. and more preferably at about 0° to about 80° C. and most preferably from about 15° to 30° C., the reaction gives acetals in good yields as shown by examples 1–4, 8 and 11 in the Table of Results. Preferably the temperature will be such that the reactants remain substantially in the liquid phase.

Additives to the reactions:

These Group VIII metal salt catalyzed reactions can be improved by carrying them out in the presence of ethylene or propylene. These materials inhibit undesirable decomposition and/or polymerization of the aldehydes and trioxanes. This is particularly true of those reactions of the shorter-chained $RCH_2CHO$ groups where R is less than four carbon atoms. Additional catalysts and/or solvents, etc. may be employed to enhance the rate of reaction and yield of products. Those skilled in the art will be familiar with such procedures.

Time:

The reaction time may also be determinative of the products formed. For instance, a comparison of examples 5, 7 and 10 of the Table of Results show that reaction times of about 1 hour or more favor the conversion of trioxanes to aldehydes, while more prolonged treatment favors the self-condensation of aldehydes to give alpha,beta-unsaturated aldehydes. The cyclotrimerization of aldehydes to trioxanes is preferably from 0.05 hours to about 24 hours, and more preferably from 0.05 hours to about 8 hours, and most preferably from 0.05 to about 5 hours. The self-condensation reactions which give alpha,beta-unsaturated aldehydes are preferably from 0.05 to 24 hours and more preferably from 0.5 to 10 hours and most preferably from 1 to 5 hours. The reaction of the aldehyde with the alcohol is characterized by more rapid reactions, which are carried out for preferably about 0.01 to about 50 hours and more preferably from about 0.25 to about 20 hours, and most preferably from about 1 to about 10 hours.

Pressure:

Generally the reaction is conducted in a sealed vessel under autogeneous pressure, although pressure may be supplied by external means and is not narrowly critical and preferably ranges from 1 to about 10,000, more preferably 1 to about 500, and most preferably 1 to about 50 atmospheres. The ethylene and propylene additives mentioned previously may be introduced to produce such pressures.

Examples:

The reactions used as examples in this application are carried out in a sealed combustion tube equipped with a magnetic stirring bar and containing a mixture of reactants and catalyst(s). The tube is immersed in an oil bath, heated to the desired temperature, and held for a period of time until reaction is essentially complete. The products are identified by gas chromatography, mass spectroscopy, nmr, and ir. While the following Table of Results is illustrative of preferred embodiments of the invention, they are not meant to limit the invention in any way.

TABLE OF RESULTS

| Example No. | Reagents - M | Catalyst - mM | Time | Temp., °C. | Conversion, %$^a$ | Products - Moles |
|---|---|---|---|---|---|---|
| 1 | Propionaldehyde - 0.086  EtOH - 0.32 | RhCl$_3$ . 3 H$_2$O - 0.38 | 5 min  16 hr | 25  100 | 52  81 | 1,1-diethoxypropane - 0.045  1,1-diethoxypropane - 0.034  2-methyl-2-pentenal - 0.018 |
| 2 | Propionaldehyde - 0.107  MeOH - 0.52 | IrCl$_3$ . 3 H$_2$O - 0.28 | 5 min  16 hr | 25  100 | 49  80 | 1,1-dimethoxypropane - 0.052  1,1-dimethoxypropane - 0.079  2-methyl-2-pentenal - 0.007 |
| 3 | Propionaldehyde - 0.093  EtOH - 0.35 | IrCl$_3$ . 3 H$_2$O - 0.28 | 5 min  16 hr | 25  100 | 34  71 | 1,1-diethoxypropane - 0.032  1,1-diethoxypropane - 0.028  2-methyl-2-pentenal - 0.019 |
| 4 | Propionaldehyde - 0.081  MeOH - 0.39 | RhCl$_3$ . 3 H$_2$O - 0.38 | 5 min  16 hr | 25  100 | 53  64 | 1,1-dimethoxypropane - 0.043  1,1-dimethoxypropane - 0.044  2-methyl-2-pentenal - 0.004 |
| 5 | Propionaldehyde - 0.131 | RhCl$_3$ . 3 H$_2$O - 0.38 | 5 hr  24 hr | 25  100 | 63  75 | triethyl-1,3,5-trioxane - 0.08  2-methyl-2-pentenal - 0.098 |
| 6 | Isobutyraldehyde - 0.03 | RhCl$_3$ . 3 H$_2$O - 0.08 | 16 hr | 25 | 95 | triisopropyl-1,3,5-trioxane - 0.28 |
| 7 | Triethyl-,3,5-trioxane | RhCl$_3$ . 3 H$_2$O | 1 hr | 100 | 100 | propionaldehyde - 0.025$^b$  2-methyl-2-pentenal - 0.075$^b$ |
| 8 | Acetaldehyde - 0.12  EtOH - 0.16 | RhCl$_3$ . 3 H$_2$O - 0.1 | 5 min | 10 | 29 | 1,1-diethoxyethane - 0.035 |
| 9 | Acetaldehyde - 0.18 | RhCl$_3$ . 3 H$_2$O - 0.15 | 5 min | 25 | 72 | trimethyltrioxane - 0.13 |
| 10 | Acetaldehyde - 0.05 | PdCl$_2$ - 0.17 | 8 hr | 100 | 90 | 2-butenal - 0.005  trimethyltrioxane - 0.005  acetic acid - 0.006 |
| 11 | Isobutyraldehyde - 0.014  MeOH | RhCl$_3$ . 3 H$_2$O - 0.08 | 2 hr | 25 | ~95 | 1,1-dimethoxy-2-methyl-propane |
| *12 | Isobutyraldehyde - 0.028 | None | 24 hr | 71 | 0 | Isobutyric acid - 0.02 |

All reactions were run in Fischer-Porter combustion tubes. The products were analyzed by nmr, ir, mass spectroscopy and gas chromatography.
$^a$Mole % Conversion
$^b$per 0.058 moles of triethyl-1,3,5-trioxane feed
*In comparison Example 12 (without catalyst) no condensation or trimerization takes place (only oxidation is observed).

Having thus disclosed the invention, what is claimed is:

1. The process for the self-condensation of aldehydes having the formula RCH$_2$CHO to form alpha,beta-unsaturated aldehydes, the improvement comprising contacting the RCH$_2$CHO with a catalytic amount of a Group VIII metal salt at $-20°$ to 300° C. wherein R is selected from hydrogen or a linear or branched-chained alkyl group having 4 or fewer carbon atoms and wherein the aldehyde is a liquid under the conditions of the reaction and the Group VIII metal salt is homogeneously dispersed in the reactant, and wherein the aldehyde undergoes self-condensation in the conjoint presence of a catalytic amount of a Group VIII metal salt and in the presence of ethylene or propylene under a pressure of 1–500 atmospheres.

2. The process of claim 1 wherein the reaction is carried out at about 80° to 300° C. for about 1–24 hours.

* * * * *